United States Patent
Justis et al.

(10) Patent No.: US 6,293,949 B1
(45) Date of Patent: Sep. 25, 2001

(54) SUPERELASTIC SPINAL STABILIZATION SYSTEM AND METHOD

(75) Inventors: Jeff R. Justis, Cordova; Michael C. Sherman, Memphis, both of TN (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/516,946

(22) Filed: Mar. 1, 2000

(51) Int. Cl.⁷ .................................................. A61B 17/56
(52) U.S. Cl. .................................................. 606/61
(58) Field of Search ........................ 606/61, 69, 70, 606/71, 76, 78, 17.11, 17.15, 17.16

(56) References Cited

U.S. PATENT DOCUMENTS

| | | | |
|---|---|---|---|
| Re. 36,221 | 6/1999 | Breard et al. . | |
| 3,786,806 | * 1/1974 | Johnson et al. | 606/78 |
| 4,364,382 | * 12/1982 | Mennen | 606/69 |
| 4,573,458 | * 3/1986 | Lower | 606/69 |
| 4,697,582 | * 10/1987 | William | 606/61 |
| 4,743,260 | 5/1988 | Burton . | |
| 4,932,975 | * 6/1990 | Main et al. | 606/61 |
| 5,041,113 | 8/1991 | Biedermann et al. . | |
| 5,092,866 | 3/1992 | Breard et al. . | |
| 5,180,381 | 1/1993 | Aust et al. . | |
| 5,180,393 | * 1/1993 | Commarmond | 606/61 |
| 5,387,213 | 2/1995 | Breard et al. . | |
| 5,415,661 | 5/1995 | Holmes . | |
| 5,423,816 | * 6/1995 | Lin | 606/61 |
| 5,597,378 | 1/1997 | Jervis . | |
| 5,601,572 | * 2/1997 | Middleman et al. | 606/78 |
| 5,616,144 | 4/1997 | Yapp et al. . | |
| 5,766,218 | 6/1998 | Arnott . | |
| 5,776,162 | 7/1998 | Kleshinski . | |
| 5,779,707 | * 7/1998 | Bertholet et al. | 606/78 |
| 5,951,558 | * 9/1999 | Fiz | 606/70 |
| 6,152,927 | * 11/2000 | Farris et al. | 606/69 |

FOREIGN PATENT DOCUMENTS 940759   7/1982 (SU) .

OTHER PUBLICATIONS

"The Use of a Memory Shape Staple in Cervical Anterior Fusion", by Olivier Ricart, Shape Memory and Superelastic Technologies ® 1997, pp. 623–626.

(List continued on next page.)

*Primary Examiner*—Gene Mancene
*Assistant Examiner*—Eduardo C. Robert
(74) *Attorney, Agent, or Firm*—Woodard, Emhardt, Naughton Moriarty & McNett

(57) ABSTRACT

A device for stabilizing at least a portion of the spinal column, including a longitudinal member sized to span a distance between at least two vertebral bodies and being at least partially formed of a shape-memory material exhibiting pseudoelastic characteristics at about human body temperature. A number of bone anchors are used to secure the longitudinal member to each of the vertebral bodies. The longitudinal member is reformed from an initial configuration to a different configuration in response to the imposition of stress caused by relative displacement between the vertebral bodies, and recovers toward the initial configuration when the stress is removed to thereby provide flexible stabilization to the spinal column. During reformation of the longitudinal member, at least a portion of the shape-memory material transforms into stress-induced martensite. In a particular aspect of the invention, the longitudinal member is a plate having a central portion at least partially formed of the shape-memory material, and a pair of connection portions disposed at opposite ends of the central portion for connection to each of the vertebral bodies. The central portion of the plate defines a number of alternating ridges and grooves along a length thereof having an initial amplitude corresponding to the initial configuration and a different amplitude corresponding to the different configuration.

55 Claims, 7 Drawing Sheets

OTHER PUBLICATIONS

"The Use of Nickel–Titanium Alloy in Orthopedic Surgery in China", by Paul Pang–Fu Kuo, MD et al., Orthopedics, Jan. 1989, vol. 12/No. 1, pp. 111–116.

"Using the Shape Recovery of Nitinol in the Harrington Rod Treatment of Scoliosis", by M.A. Schmerling et al., vol. 10, pp. 879–892, 1976.

"Medical Applications of Ni–Ti Alloys in China", by Shibi Lu, M.D., pp. 445–451.

The Use of Ni–Ti as an Implant Material in Orthopedics, by Dr. J. Haasters, Prof. G. v.Salis–Solio, & Dr. G. Bensmann, pp. 426–444.

"Shape Memory and Super–elasticity Effects NiTi Alloys", by Yuichi Suzuki, Excerpt from Titanium and Zirconium, vol. 30, No. 4, Oct. 1982.

"TiNi–alloy with super elasticity", (Tranplantation of the human malignant bone and soft part tumors to nude mice), *Orthopedic Surgery*, vol. 32, No. 1, Jan. 1981.

SMST–97, Proceedings of the Second International conference on Shape Memory and Superelastic Technologies, Mar. 2–6, 1997.

* cited by examiner-

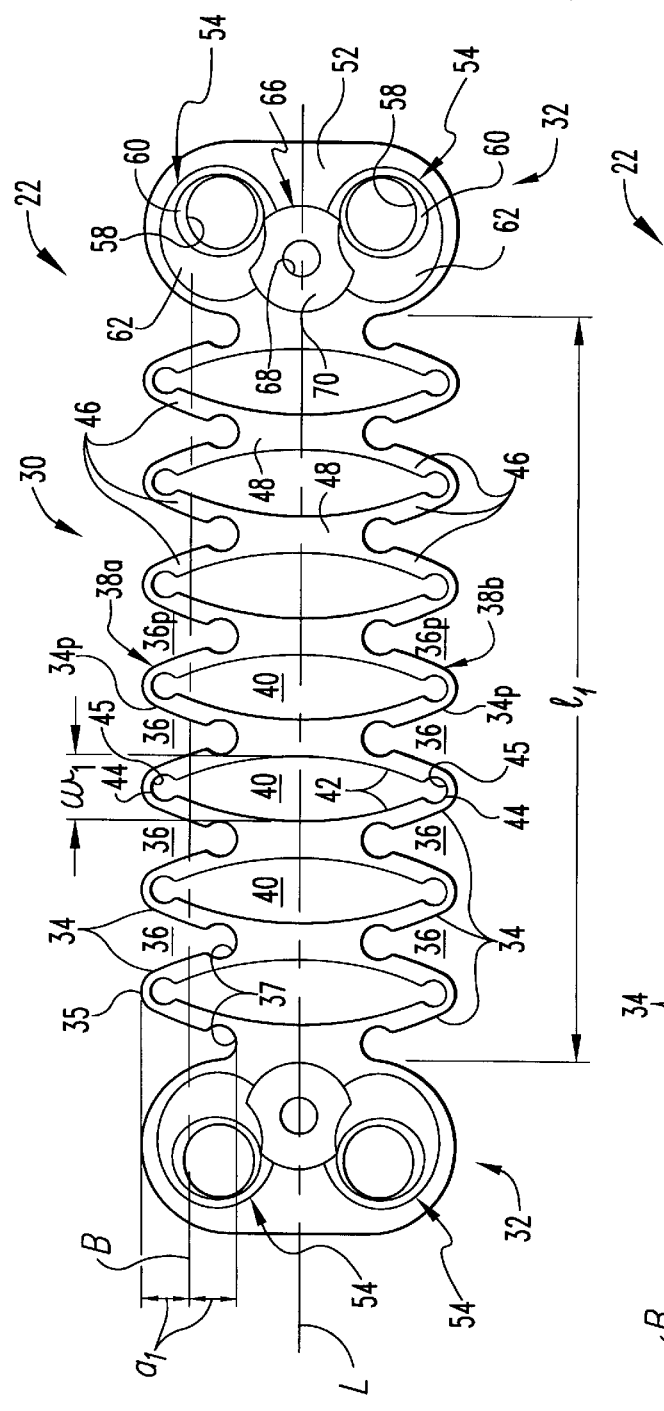
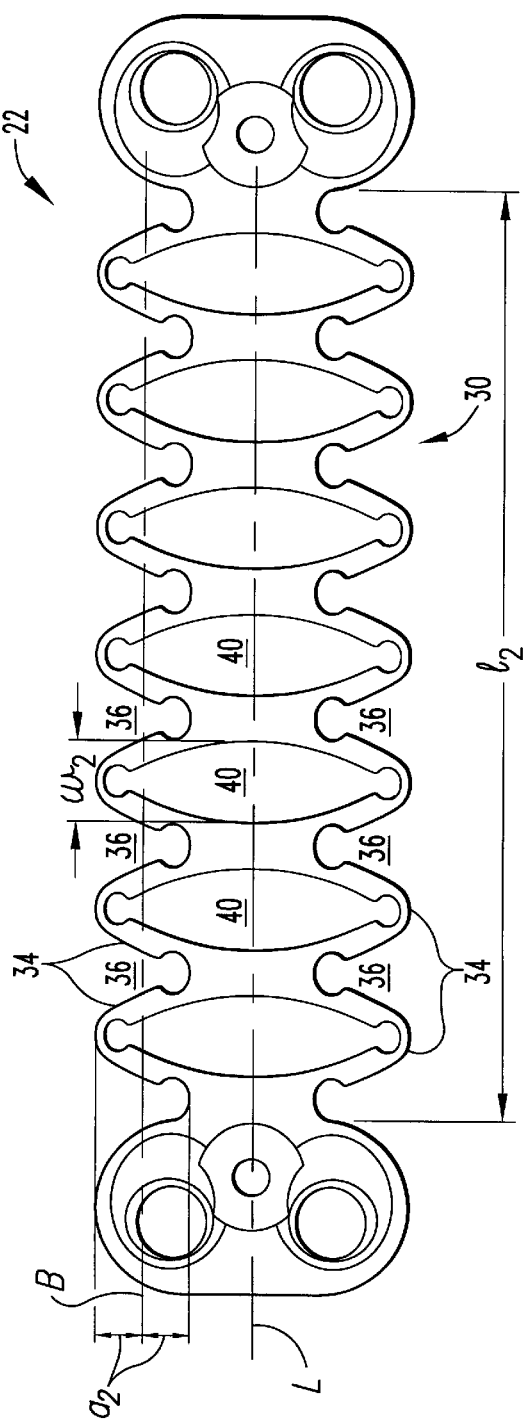
Fig. 4a
Fig. 4b

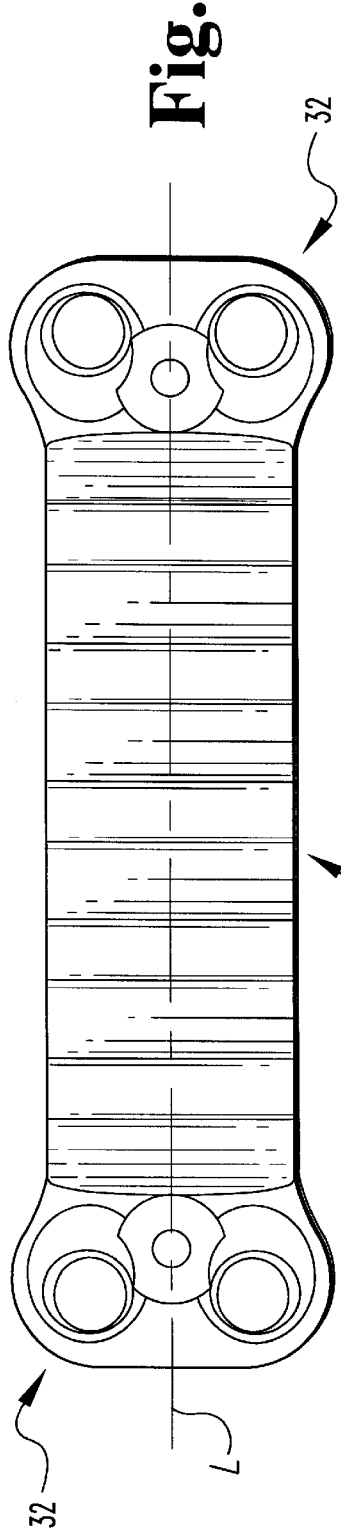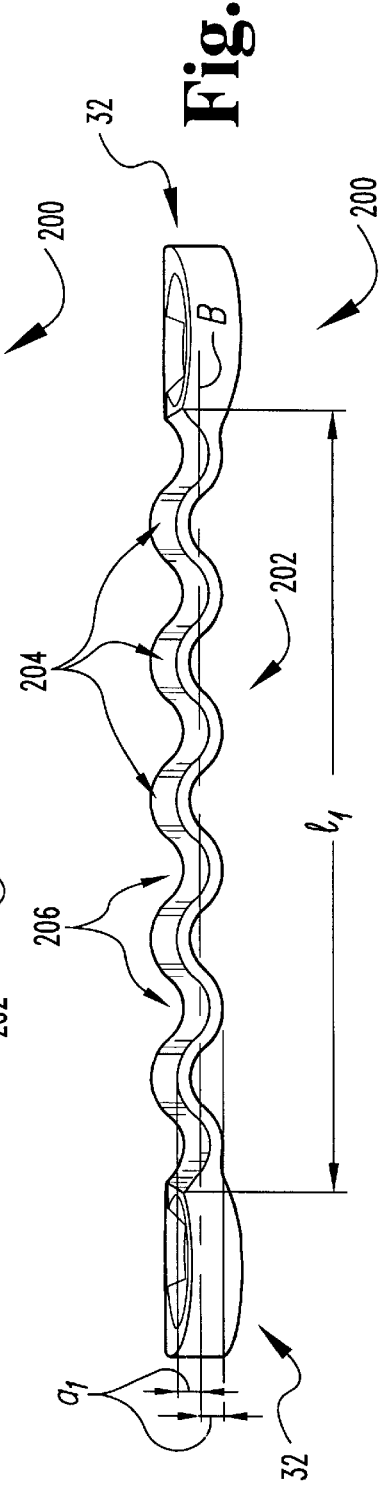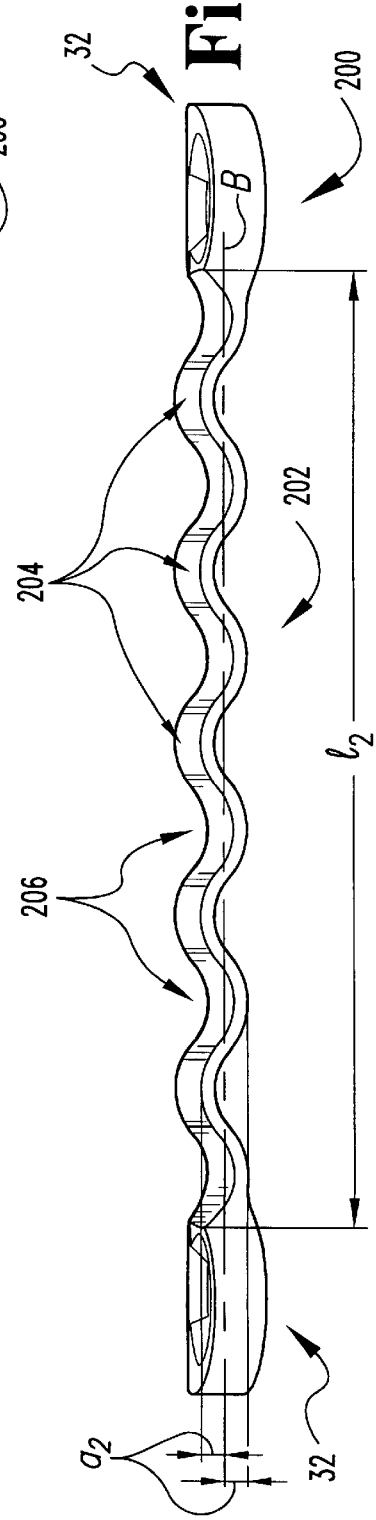

SUPERELASTIC SPINAL STABILIZATION SYSTEM AND METHOD

FIELD OF THE INVENTION

The present invention relates generally to the field of instrumentation and systems for treatment of the spine, and more particularly to a device for flexibly stabilizing the cervical spine.

BACKGROUND OF THE INVENTION

As with any bony structure, the spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two adjacent vertebrae and the disc tissue or disc space therebetween), and especially those affecting disc tissue, it has long been known to remove some or all of a degenerated, ruptured or otherwise failing disc. In cases in which intervertebral disc tissue is removed or is otherwise absent from a spinal motion segment, corrective measures are indicated to insure the proper spacing of adjacent vertebrae formerly separated by the removed disc tissue.

Commonly, the adjacent vertebrae are fused together using a graft structure formed of transplanted bone tissue, an artificial fusion element, or other suitable compositions. Elongated rigid plates have been helpful in the stabilization and fixation of the spine when used alone or in conjunction with a grafting procedure, especially in the thoracic and lumbar regions of the spine. These plating systems also have the potential advantage of increasing union rates, decreasing graft collapse, minimizing subsequent kyphotic deformity, and decreasing the need for bulky or rigid postoperative immobilization. Additionally, rigid internal fixation systems may improve the overall quality of life of the patient and may provide the opportunity for earlier rehabilitation.

The plating techniques described above have also found some level of acceptance by surgeons specializing in the treatment of the cervical spine. The cervical spine can be approached either anteriorly or posteriorly, depending upon the spinal disorder or pathology to be treated. Many well-known surgical exposure and fusion techniques of the cervical spine are described in the publication entitled *Spinal Instrumentation*, edited by Drs. Howard An and Jerome Cotler. The primary focus of cervical plating systems has been to restore stability and increase the stiffness of an unstable spinal motion segment. During the development of cervical plating systems, various needs have been recognized. For example, the system should provide strong mechanical fixation that can control movement of the vertebral segments. The system should also be able to maintain stress levels below the endurance limits of the plate material, while at the same time exceeding the strength of the anatomic structures or vertebrae to which the plating system is engaged. Additionally, the system should preferably be capable of accommodating for the natural movement of the vertebrae relative to one another, including torsional movement during rotation of the spine and translational movement during flexion or extension of the spine.

There is increased concern in the spinal medical community that anterior or posterior plating systems may place excessive loads on the vertebrae or graft structure in response to small degrees of spinal motion. See, e.g., K. T. Foley, D. J. DiAngelo, Y. R. Rampersaud, K. A. Vossel and T. H. Jansen, *The In Vitro Effects of Instrumentation on Multi-level Cervical Strut-Graft Mechanics*, 26th Proceeding of the Cervical Spine Research Society, 1998. If the plating system is used in conjunction with grafting, these loads may promote pistoning, which can ultimately lead to degradation or failure of the graft construct. Additionally, even small degrees of spinal motion can cause significant forces to be placed on the spinal plate and the bone anchor devices which attach the plate to the vertebrae, whether they be bone screws, hooks, etc. These forces may lead to failure of the plate or loosening of the points of attachment between the bone anchors and the vertebrae, thus resulting in the potential loss of support by the plate.

Thus, there is a general need in the industry to provide a device for flexibly stabilizing the spine, and in particular the cervical region of the spine. The present invention meets this need and provides other benefits and advantages in a novel and unobvious manner.

SUMMARY OF THE INVENTION

The present invention relates generally to a system for flexibly stabilizing the spine, and more particularly the cervical region of the spine. While the actual nature of the invention covered herein can only be determined with reference to the claims appended hereto, certain forms of the invention that are characteristic of the preferred embodiments disclosed herein are described briefly as follows.

In one form of the present invention, a device is provided for stabilizing at least a portion of the spinal column. The device includes a longitudinal member sized to span a distance between at least two vertebral bodies and being at least partially formed of a shape-memory material exhibiting pseudoelastic characteristics when implanted within the body. The device also includes bone anchors for securing the longitudinal member to each of the vertebral bodies. The longitudinal member is reformed from an initial configuration to a different configuration in response to the imposition of stress caused by relative displacement between the vertebral bodies and recovers toward the initial configuration when the stress is removed.

In another form of the present invention, a device is provided for stabilizing at least a portion of the spine. The device includes a compliant element at least partially formed of a pseudoelastic shape-memory material displaying reversible stress-induced martensitic behavior at about human body temperature. The compliant element has a length sized to span a distance between at least two spinal motion segments and is secured to each of the spinal motion segments by at least two anchoring elements. The length of the compliant element is variable between an initial length and a different length through the imposition of stress caused by relative displacement between the spinal motion segments, with the different length occurring through the transformation of at least a portion of the pseudoelastic shape-memory material into reversible stress-induced martensite, and with the compliant element recovering or reforming toward the initial length when the stress is removed.

In yet another form of the present invention, a spinal stabilization system is provided, comprising an elongate member for placement adjacent the cervical region of the spine and being at least partially formed of a pseudoelastic shape-memory material displaying reversible stress-induced martensitic behavior at about human body temperature. The system is further comprised of at least two bone engaging members, each adapted to engage a respective one of at least two cervical vertebrae to secure the elongate member thereto. The elongate member is deformed during relative displacement between the cervical vertebrae, thus transforming a portion of the shape-memory material into a stress-induced martensitic state. The elongate member exerts a substantially constant restorative force on the cervical vertebrae when the shape-memory material is in the stress-induced martensitic state to thereby flexibly stabilize the cervical region of the spine.

In still another form of the present invention, a connector apparatus is provided for connecting a first member to a second member. The apparatus is comprised of a central portion having a longitudinal axis and being at least partially formed of a shape-memory material exhibiting pseudoelastic characteristics at about body temperature. The central portion includes a number of alternating ridges and grooves disposed along the longitudinal axis. The apparatus also includes at least two connection portions, each configured to engage a respective one of the first and second members. The ridges and grooves are transformed from an initial configuration to a different configuration in response to the imposition of stress caused by relative displacement between the first and second members, and are reformed toward the initial configuration when the stress is removed.

In a further form of the present invention, a method is provided for stabilizing at least a portion of the spinal column including at least two vertebrae. The method includes: providing an elongate member having a length extending between the two vertebrae and being at least partially formed of a pseudoelastic shape-memory material displaying reversible stress-induced martensitic behavior at about body temperature; securing the elongate member to the two vertebrae; transforming at least a portion of the shape-memory material into a martensitic state as a result of the imposition of the stress onto the elongate member during relative movement between the two vertebrae; and applying a substantially constant restorative force to the two vertebrae when the shape-memory material is in the martensitic state to provide stabilization to the at least a portion of the spinal column.

It is one object of the present invention to provide a device and method for stabilizing at least a portion of the spine, and more particularly the cervical region of the spine.

Further objects, features, advantages, benefits, and aspects of the present invention will become apparent from the drawings and description contained herein.

BRIEF DESCRIPTION OF THE DRAWINGS

FIG. 4a is a top view of a stabilization plate according to an embodiment of the present invention, shown in an unstressed configuration.

FIG. 4b is a top view of the stabilization plate depicted in FIG. 4a, shown in a stressed configuration.

FIG. 5 is a side elevation view of the stabilization plate depicted in FIG. 4a.

FIG. 6 is an end elevation view of the stabilization plate depicted in FIG. 4a.

FIG. 7 is an angled cross-sectional view of the stabilization plate depicted in FIG. 4a, taken along line 7—7 of FIG. 4a.

FIG. 10 is a top view of a stabilization plate according to another embodiment of the present invention.

FIG. 11a is a side elevation view of the stabilization plate depicted in FIG. 10, shown in an unstressed configuration.

FIG. 11b is a side elevation view of the stabilization plate depicted in FIG. 10, shown in a stressed configuration.

DESCRIPTION OF THE ILLUSTRATED EMBODIMENTS

Figure 1:
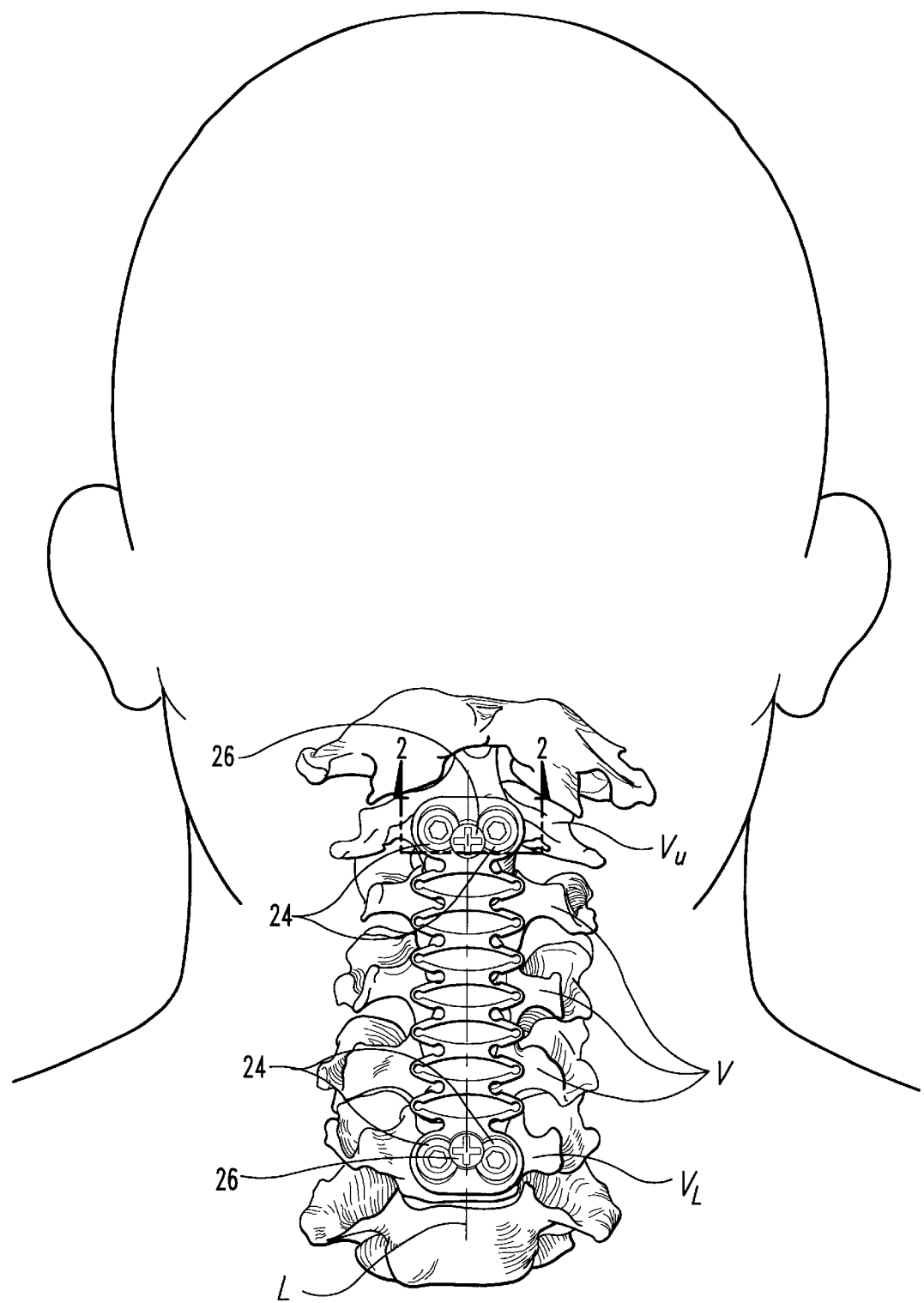
FIG. 1 is an anterior view of the cervical region of the spine showing a spinal stabilization system according to one embodiment of the present invention attached to two cervical vertebrae.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 2:
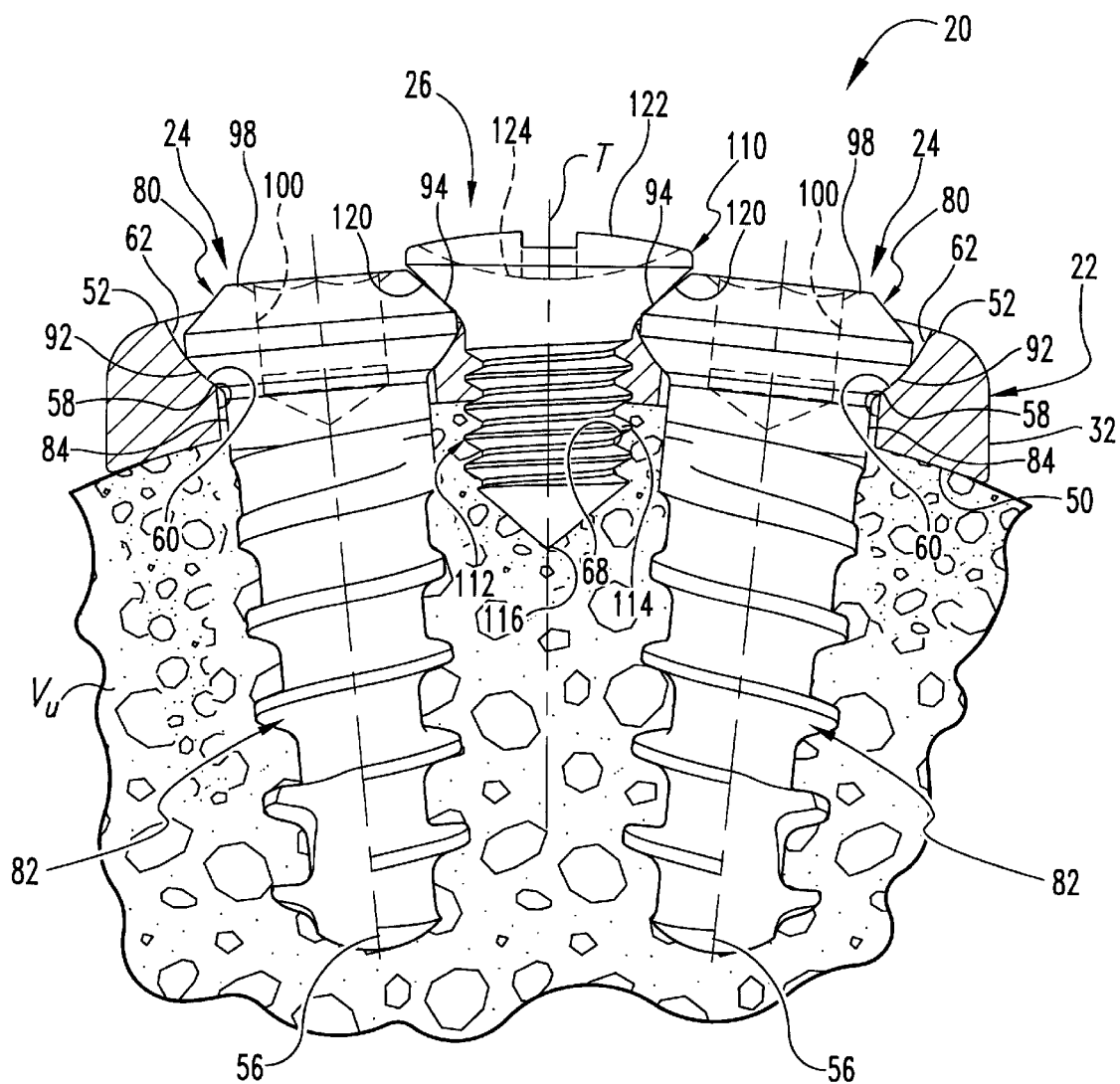
FIG. 2 is a partial cross-sectional view of the spinal stabilization system depicted in FIG. 1, with the screws disposed through holes in the stabilization plate and engaged to a cervical vertebra.
Figure 3:
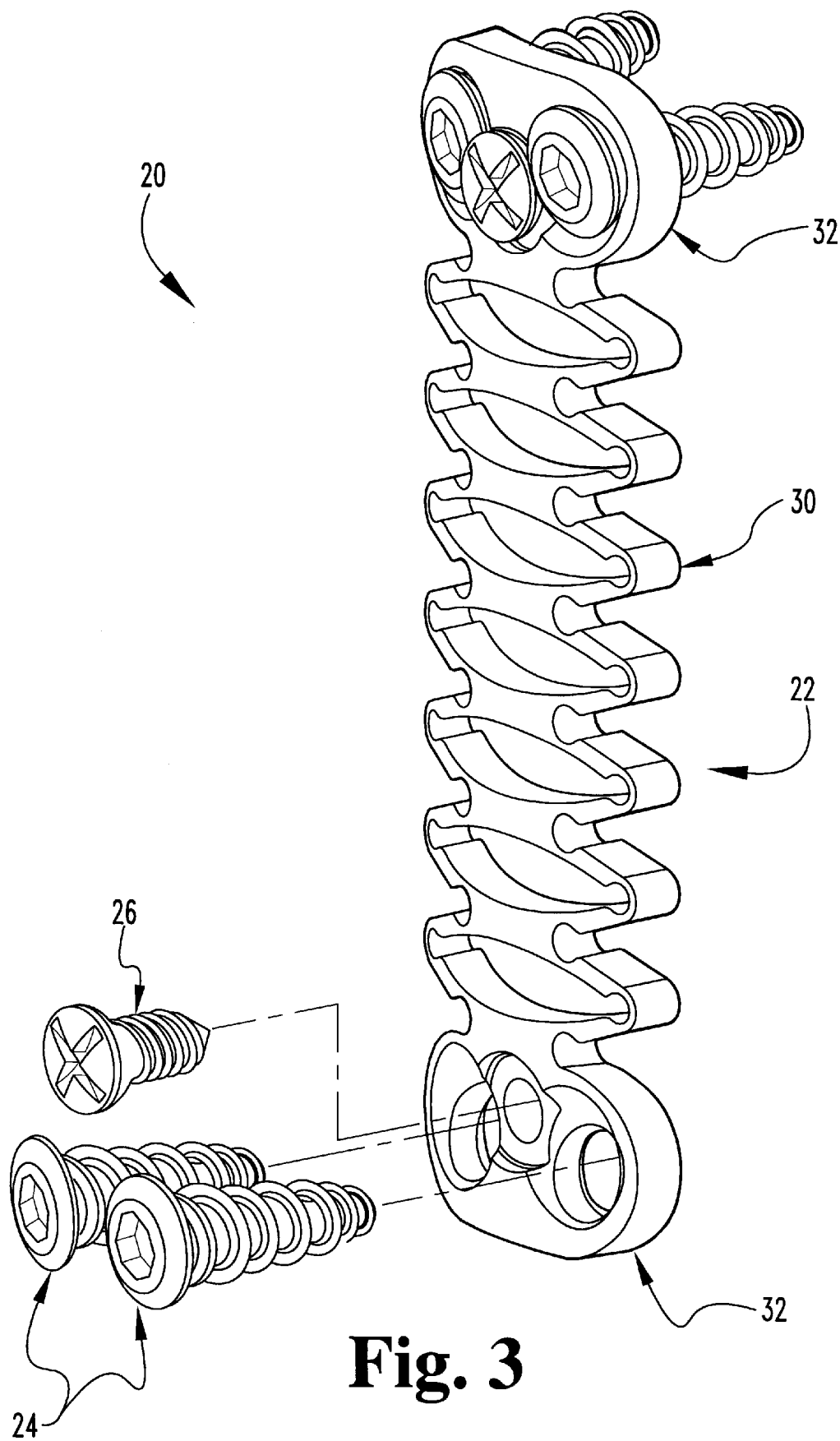
FIG. 3 is a side perspective view of the spinal stabilization system depicted in FIG. 1.

FIGS. 1–2 depict a spinal stabilization system 20 according to one embodiment of the present invention for stabilizing at least a portion of the vertebral column. Stabilization system 20 is shown attached to the cervical region of the vertebral column, extending across a plurality of spinal motion segments, such as cervical vertebrae V. However, it should be understood that system 20 may also be utilized in other areas of the spine, such as the thoracic, lumbar, lumbo sacral and sacral regions of the spine. It should also be understood that system 20 can extend across any number of vertebrae V, including two adjacent vertebrae V. Additionally, although system 20 is shown as having application in an anterior approach, system 20 may alternatively be applied in other surgical approaches, such as, for example, a posterior approach.

In a typical grafting procedure, one or more adjacent pairs of vertebra V may be fused together by way of a graft or implant (not shown) positioned in the disc space between the adjacent vertebrae V. The implant may be a bone graft, an artificial fusion device, or any other type of interbody device that is insertable into the disc space to promote fusion between the adjacent vertebrae V. One purpose of the stabilization system 20 is to prevent excessive loads from being placed on the graft structures in response to even small degrees of spinal motion. However, it should be understood that stabilization system 20 can be used in conjunction with fusion or non-fusion treatment of the spine.

In accordance with the present invention, stabilization system 20 includes an elongate member 22 positioned along a portion of the vertebral column. In the illustrated embodiment, the longitudinal member is an elongated stabilization plate sized to span a distance between at least two vertebrae V. Although elongate member 22 has been illustrated and described as a spinal plate, it should be understood that elongate member 22 can also be configured as a spinal rod or any other type of longitudinal element for use in conjunction with a spinal fixation system. It should also be understood that any number of plates 22, including a pair of plates 22 positioned on opposite sides of the spine, could be used to provide stabilization to the vertebral column. Stabilization plate 22 is secured to the upper and lower vertebrae $V_U$, $V_L$ (FIG. 1) by a plurality of bone anchors, shown in the form of bone screws 24. However, other types of bone anchors are also contemplated, such as, for example, spinal hooks. A locking device 26 engages the adjacent bone screws 24 to prevent bone screws 24 from loosening and backing out. In the illustrated embodiment, the locking device 26 is a screw extending through each end portion of the plate 22 and into engagement with the heads of adjacent bone screws 24. However, other types of locking devices are also contemplated, such as, for example, a pop rivet, a retainer fabricated from a shape-memory alloy configured to change shape in response to a change in temperature or the release of stress, a locking washer rotatably displaceable between an unlocked position and a locked position, or any other type of locking mechanisms known to those of skill in the art. An example of a locking washer for use with the present invention is disclosed in U.S. patent application Ser. No. 09/399,525 entitled "Anterior Cervical Plating System" filed on Sep. 20, 1999, the contents of which are hereby incorporated by reference. Further details regarding spinal stabilization system 20 are described more fully below.

Referring to FIGS. 3–7, shown therein are various details regarding the stabilization plate 22. Plate 22 has a longitudinal axis L extending along its length and includes an elongated central portion 30 and a pair of connection portions 32 disposed at opposite ends of central portion 30. In the illustrated embodiment, central portion 30 and connection portions 32 are formed integral to plate 22, thus forming a unitary structure or construct. However, it should be understood that connection portions 32 can be formed separate from central portion 30 and attached thereto by any method known to one of ordinary skill in the art, such as, for example, by fastening or welding. Plate 22 is at least partially formed of a shape-memory material that exhibits pseudoelastic characteristics or behavior at about human body temperature, the details of which will be discussed below. It should be understood that the terms "pseudoelastic" and "superelastic" have identical meanings and are used interchangeably throughout this document. In one embodiment of the present invention, the entire plate 22 is formed of the shape-memory material. However, it should be understood that only central portion 30 need be at least partially formed of the shape-memory material, with the connection portion 32 being formed of any suitable biocompatible material, such as, for example, stainless steel or titanium.

SMAs exhibit a "shape-memory" characteristic or behavior in which a particular component formed of a shape-memory alloy ("SMA") is capable of being deformed from an initial "memorized" shape or configuration to a different shape or configuration, and then reformed back toward its initial shape or configuration. The ability to possess shape-memory is a result of the fact that the SMA undergoes a reversible transformation from an austenitic state to a martensitic state. If this transformation occurs due to a change in temperature, the shape-memory phenomena is commonly referred to as thermoelastic martensitic transformation. However, if the martensitic transformation occurs due to the imposition of stress, the shape-memory phenomena is commonly referred to as stress-induced martensitic transformation. The present invention is primarily concerned with stress-induced martensitic transformation.

SMAs are known to display a superelastic phenomena or rubber-like behavior in which a strain attained beyond the elastic limit of the SMA material during loading is recovered during unloading. This superelastic phenomena occurs when stress is applied to an SMA article at a temperature slightly higher than the temperature at which the SMA begins to transform into austenite (sometimes referred to as the transformation temperature or $A_s$). When stressed, the article first deforms elastically up to the yield point of the SMA material (sometimes referred to as the critical stress). However, upon the further imposition of stress, the SMA material begins to transform into stress-induced martensite or "SIM". This transformation takes place at essentially constant stress, up to the point where the SMA material is completely transformed into martensite. When the stress is removed, the SMA material will revert back into austenite and the article will return to its original, pre-programmed programmed or memorized shape. This phenomena is sometimes referred to as superelasticity or pseudoelasticity. It should be understood that this phenomena can occur without a corresponding change in temperature of the SMA material. Further details regarding the superelastic phenomena and additional characteristics of SIM are more fully described by Yuichi Suzuki in an article entitled *Shape Memory Effect and Super-Elasticity in Ni-Ti Alloys*, Titanium and Zirconium, Vol. 30, No. 4, October 1982, the contents of which are hereby incorporated by reference.

There is a wide variety of shape-memory materials suitable for use with the present invention, including shape-memory metal alloys (e.g., alloys of known metals, such as, for example, copper and zinc, nickel and titanium, and silver and cadmium) and shape-memory polymers. While there are many alloys which exhibit shape-memory characteristics, one of the more common SMAs is an alloy of nickel and titanium. One such alloy is nitinol, a bio-compatible SMA formed of nickel and titanium. Nitinol is well suited for the particular application of the present invention because it can be programmed to undergo a stress-induced martensitic transformation at about normal human body temperature (i.e., at about 35–40 degrees Celsius). Moreover, nitinol has a very low corrosion rate and excellent wear resistance, thereby providing an advantage when used as a support structure within the human body. Additionally, implant studies in animals have shown minimal elevations of nickel in the tissues in contact with the nitinol material. It should be understood, however, that other SMA materials that exhibit superelastic characteristics are contemplated as being within the scope of the invention.

The central portion 30 of plate 22 is at least partially formed of an SMA material and has an initial or "memorized" shape or configuration (see FIG. 4a), and a different shape or configuration (FIG. 4b) when deformed through the imposition of stress onto plate 22. If the central portion 30 is reshaped or deformed while at a temperature above the transformation temperature $A_s$, the central portion 30 will automatically recover toward its initial shape or configuration when the stress is removed from plate 22. In one embodiment of the present invention, the plate 22 is secured to the upper and lower vertebrae $V_u$, $V_l$ while in a substantially unstressed initial configuration where virtually all of the SMA material is in an austenitic state. Upon the imposition of stress onto plate 22, caused by relative movement between the upper and lower vertebrae $V_u$, $V_l$, at least a portion of the SMA material is transformed into reversible stress-induced martensite. Upon the reduction or removal of stress, at least a portion of the SMA material is transformed back into austenite. It should be understood that the plate 22 may be pre-stressed prior to being secured to the upper and lower vertebrae $V_u$, $V_l$, thus initially transforming a portion of the SMA material from austentite into SIM. In this case, the SMA material will never attain an entirely austenitic state when the stress imposed onto plate 22 by the upper and lower vertebrae $V_u$, $V_l$ is removed.

Referring specifically to FIG. 4a, central portion 30 is shown in an initial, unstressed configuration. Central portion 30 has an accordion-like shape, defining a series of alternating ridges 34 and grooves 36 extending along longitudinal axis L and facing laterally outward relative to longitudinal axis L. When in its initial configuration, central portion 30 has an initial, unstressed length $l_1$. Preferably, each of the alternating ridges 34 and grooves 36 has a substantially triangular shape, with the outermost tip 35 of ridges 34 being rounded to avoid trauma to adjacent tissue, and the innermost portion of grooves 36 defining a partially cylindrical surface 37. However, it should be understood that ridges 34 and grooves 36 can take on other shapes as well, such as, for example, an arcuate shape, an undulating curve shape, or a square or rectangular shape. When central portion 30 is in its initial configuration, each of the ridges 34 and grooves 36 have an initial amplitude $a_l$, as measured from base line B to the outermost tip 35 and the innermost point of cylindrical surface 37. Preferably, the partially cylindrical surface 37 has a diameter somewhat larger than the minimum distance between adjacent ridges 34.

In the illustrated embodiment, a number of the alternating ridges 34 and grooves 36 are defined along each of the laterally facing sides 38a, 38b of central portion 30, with the ridges and grooves defined along side 38a being disposed laterally opposite respective ones of the ridges and grooves defined along side 38b, thereby defining laterally opposing pairs of ridges 34p and laterally opposing pairs of grooves 36p. A number of openings or slots 40 extend through central portion 30 intermediate the laterally opposing pairs of ridges 34p. Preferably, slots 40 have a substantially oval shape, with each of the slots 40 having laterally extending side walls defining opposing concave surface 42 and an initial slot width $w_l$ when central portion 30 is in its initial, unstressed configuration. However, it should be understood that slots 40 can take on other shapes as well, such as, for example, circular, elliptical, diamond or other geometric shapes as would occur to one of ordinary skill in the art. Slots 40 span virtually the entire distance between the opposing pairs of ridges 34p, having opposing ends 44 positioned proximately adjacent the outermost tips 35 of opposing pairs of ridges 34p. In a preferred embodiment, the opposing ends 44 of slots 40 each define a partially cylindrical surface 45. Preferably, the partially cylindrical surface 45 has a diameter somewhat larger than the minimum distance between the opposing concave surfaces 42. The configuration of central portion 30 can alternatively be described as having a pair of laterally opposing thin strips of material 46 extending along longitudinal axis L, each having a zig-zag or corrugated shape and being linked together by a number of laterally extending linking portions 48.

Referring now to FIG. 4b, central portion 30 is shown reformed from the initial shape or configuration illustrated in FIG. 4a to a different, stressed shape or configuration, such reformation occurring in response to the imposition of stress caused by relative displacement between the upper and lower vertebrae $V_u$, $V_l$ (FIG. 1). This relative displacement can arise through translational movement of upper and lower vertebrae $V_u$, $V_l$, as occurring during either flexion or extension of the spinal column, or through torsional movement, as occurring during rotation of the spinal column. The imposition of stress onto central portion 30 causes at least a portion of the shape-memory material to transform into reversible stress-induced martensite. When deformed into its different configuration, central portion 30 has a different, stressed length $l_2$, ridges 34 and grooves 36 have a different amplitude $a_2$, and slots 40 are reshaped to define a different slot width $w_2$. In the illustrated embodiment, central portion 30 is elongated or lengthened when stressed, thus increasing length $l_2$ and slot width $w_2$ while decreasing the amplitude $a_2$. However, it should be understood that central portion 30 could alternatively be compressed or shortened when stressed, thus decreasing length $l_2$ and slot width $w_2$ while increasing the amplitude $a_2$.

Figure 7:
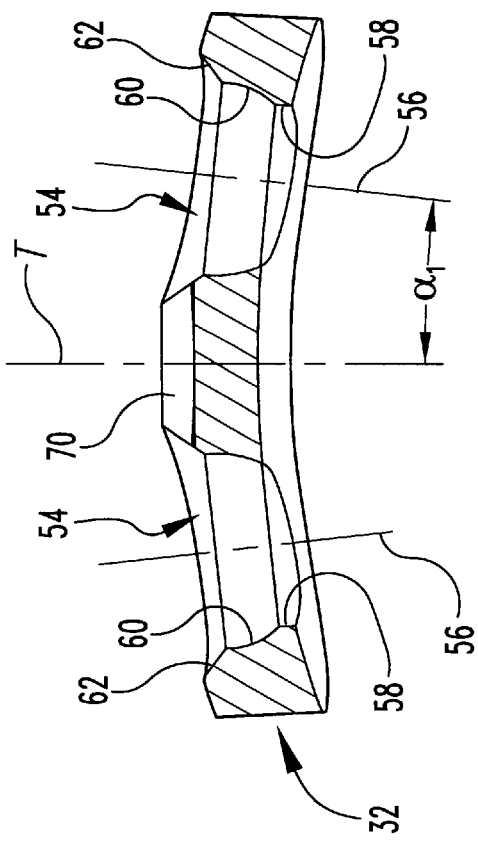
Figure 6:
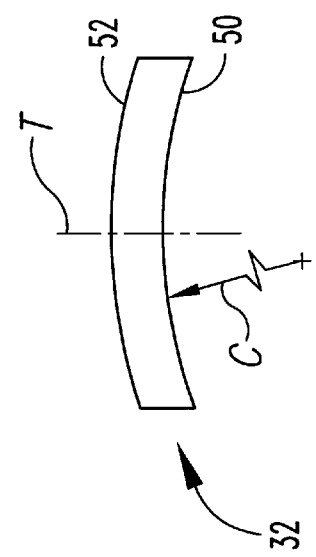

Referring collectively to FIGS. 4a and 7, shown therein are various details regarding the connection portions 32. Each of the connection portions 32 has an inner surface 50 and an oppositely facing outer surface 52. When plate 22 is secured to the spinal column (FIGS. 1 and 2), the inner surface 50 abuts the upper and lower vertebrae $V_u$, $V_l$. Inner surface 50 defines a concave lateral curvature C (FIG. 6) extending along the longitudinal axis L. Lateral curvature C preferably corresponds to the anatomical curvature of the anterior, outer surfaces of upper and lower vertebrae $V_u$, $V_l$. Outer surface 52 preferably defines a convex surface extending along longitudinal axis L to reduce the amount of trauma to the adjacent soft tissue when plate 22 is secured to the spinal column. Preferably, the central portion 30 of plate 22 defines a corresponding concave lateral curvature C along inner surface 51 and a corresponding convex outer surface 53. However, it should be understood that the central portion 30 and the connection portions 32 can be individually configured to accommodate the specific spinal anatomy and vertebral pathology involved in any particular application of stabilization system 20.

Figure 5:
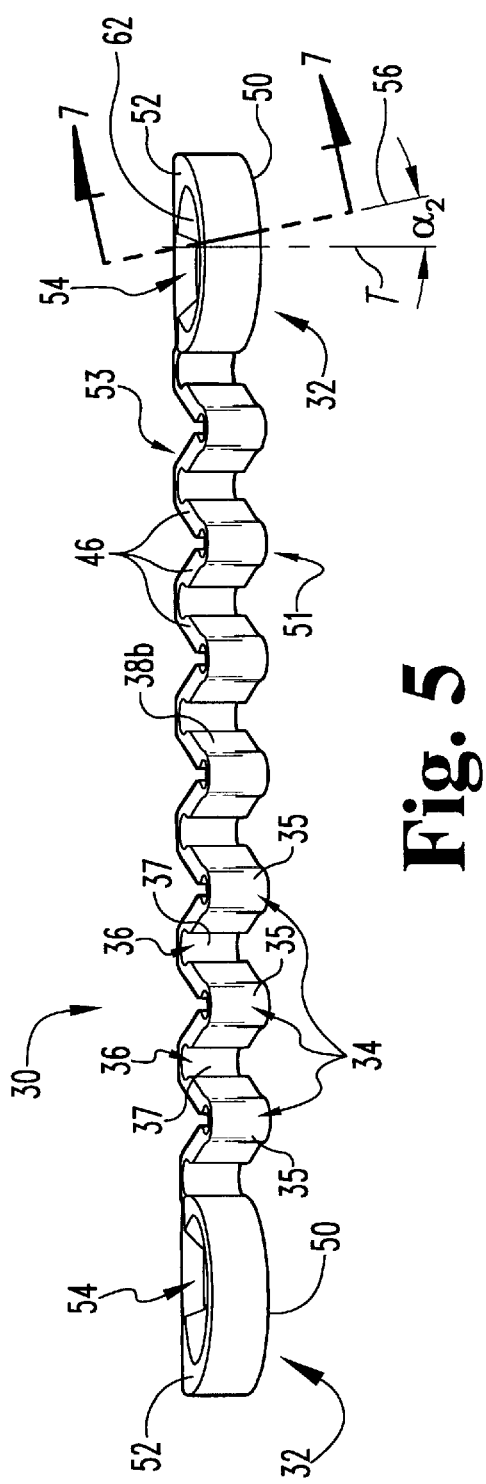

Each of the connection portions 32 includes a pair of openings 54 extending between the inner and outer surfaces 50, 52 along an axis 56 and configured to receive a respective one of the bone screws 24 therein. In the illustrated embodiment, the axis 56 of openings 54 extends inwardly toward transverse axis T at an angle $\alpha_1$ (FIG. 7) and outwardly toward the end of connection portion 32 at an angle $\alpha_2$ (FIG. 5). In one specific embodiment, angle $\alpha_1$ is approximately 6 degrees and angle $\alpha_2$ is approximately 12 degrees; however, other angles $\alpha_1, \alpha_2$ are also contemplated as being within the scope of the present invention. Preferably, openings 54 are identical in size and configuration, and are located symmetrically about longitudinal axis L. However, it should be understood that other sizes and configurations of openings 54 are also contemplated and that a single opening 54 could alternatively be defined in each of the connection portions 32. Each of the openings 54 includes a cylindrical bore 58, extending through connection portion 32 along axis 56 and opening onto the inner surface 50. Openings 54 also include a partially spherical recess 60, extending from cylindrical bore 58 toward outer surface 52 along axis 56. Openings 54 additionally include a conical portion 62, extending between spherical recess 60 and outer surface 52 along axis 56. Preferably, conical portion 62 is flared outwardly at approximately 45 degrees relative to axis 56.

Each of the connection portions 32 also includes a fastener bore 66 extending between the inner and outer surfaces 50, 52 along transverse axis T and preferably intersecting the longitudinal axis L to thereby position fastener bore 66 intermediate and laterally adjacent bone screw openings 54. Fastener bore 66 is adapted to receive a respective one of the locking fasteners 26 therein. Specifically, fastener bore 66 includes a threaded portion 68 opening onto the inner surface 50 and a conical portion 70 extending between the threaded portion 68 and the outer surface 52. However, it should be understood that other configurations of fastener bore 66 are also contemplated. For example, fastener bore 66 need not necessarily extend entirely through connection portion 32 in that threaded portion 68 can stop short of inner surface 50.

Figure 8:
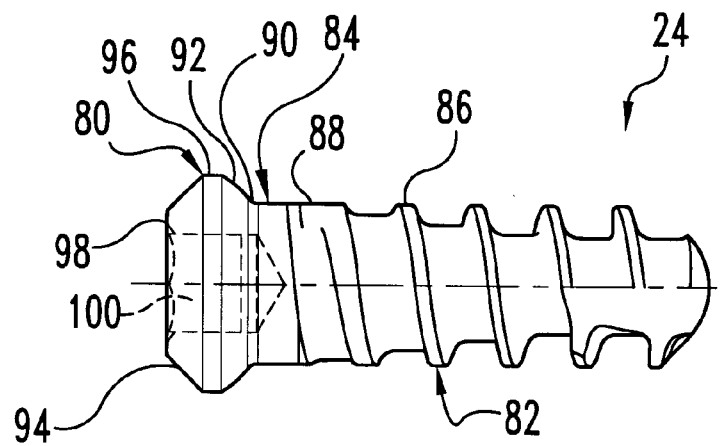
FIG. 8 is a side elevation view of a bone screw according to one aspect of the present invention.

Referring to FIG. 8, shown therein are various details regarding bone screw 24. Bone screw 24 includes a head portion 80 connected to a threaded shank portion 82 by an intermediate portion 84. Threaded shank portion 82 defines a number of threads 86 configured to engage vertebral bone and sized to pass through the cylindrical bore 58 in connection portion 32. Threads 86 are preferably cancellous threads, configured for engagement in the cervical region of the spinal column. Additionally, threads 86 may be configured to be self-tapping. Further, threads 86 preferably define a constant outer diameter along the length of threaded portion 82 approximately equal to the outer diameter of intermediate portion 84, and a root diameter that tapers inwardly toward the intermediate portion 84. However, it should be understood that other configurations of threaded portion 82 are also contemplated as would occur to one of ordinary skill in the art.

The threads 86 gradually transition into intermediate portion 84 by way of a thread run out 88. Intermediate portion 84 has an outer diameter sized somewhat larger than the diameter of the cylindrical bore 58 in connection portion 32. Intermediate portion 84 transitions into head portion 80 by way of a chamfer 90. Head portion 80 includes a lower, partially spherical surface 92 configured to be substantially complementary to the partially spherical recess 60 of opening 54. Head portion 80 also includes an upper conical surface 94, connected to spherical surface 92 by a flattened shoulder 96. In one embodiment, conical surface 94 is flared inwardly relative to shoulder 96 at approximately 45 degrees. Head portion 80 further includes a truncated or flattened upper surface 98, through which extends a tool receiving recess 100 configured to receive a driving tool therein (not shown). In one embodiment, the tool recess 100 is a hexagonal recess; however, other shapes are also contemplated as would occur to those skilled in the art.

Figure 9:
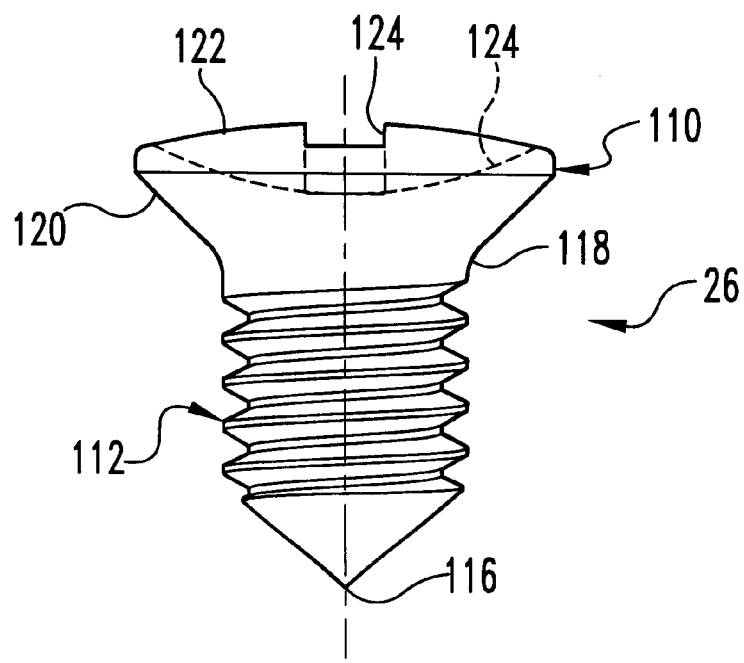
FIG. 9 is a side elevation view of a locking fastener according to another aspect of the present invention.

Referring to FIG. 9, shown therein are various details regarding locking fastener 26. Locking fastener 26 includes a head portion 110 and a threaded shank portion 112 extending therefrom. Threaded shank portion 112 defines a number of machine threads 114, configured to engage the threaded portion 68 of fastener bore 66 in connection portion 32. Threaded shank portion 112 terminates in a sharp point 116 to facilitate insertion of locking fastener 26 into fastener bore 66 and to permit easier penetration into the upper and lower vertebrae $V_u$, $V_l$. Threaded shank portion 112 transitions into head portion 110 by way of an outward taper 118. Head portion 110 includes a lower, conical surface 120 configured substantially complementary to the upper conical surface 94 of bone screw 24. In one embodiment, conical surface 120 is flared outwardly at approximately 45 degrees. Head portion 110 further includes an upper surface 122, through which extends a tool receiving recess 124 configured to receive a driving tool therein (not shown). In one embodiment, the tool recess 124 is a Phillips-type recess; however, other types are also contemplated as would occur to those skilled in the art.

Referring once again to FIGS. 1 and 2, shown therein is spinal stabilization system 20 securely attached to the upper and lower vertebrae $V_u$, $V_l$. Initially, plate 22 is positioned across at least two vertebrae V, with the inner surface 50 of the connection portions 32 placed in abutment against an outer surface of the upper and lower vertebrae $V_u$, $V_1$. The connection portions 32 are then secured to the upper and lower vertebrae $V_u$, $V_l$ by passing bone screws 24 through openings 54 and driving threaded portion 82 into vertebral bone by way of a driver (not shown) inserted in tool receiving recess 100. The bone screws 24 continue to be driven into vertebral bone until the lower spherical surface 92 of the head portion 80 is placed in abutment against the upwardly facing spherical recess 60 of opening 54.

Conical portion 62 of openings 54 serves to facilitate the insertion of bone screws 24 into openings 54. Further, the interaction between spherical surface 92 and spherical recess 60 allows the bone screw 24 to be oriented relative to axis 56 within a range of angles, limited by the interference between the intermediate portion 84 of bone screw 24 and the cylindrical bore 58 in connection portion 32. Openings 54 act as a countersink for the head portion 80 of bone screws 24, allowing a significant portion of head portion 80 to be disposed beneath the upper surface 52 of connection portion 32 to thereby minimize the overall height or profile of plate 22.

After the bone screws 24 are driven into the upper and lower vertebrae $V_u$, $V_l$, thereby securely attaching plate 22 thereto, the locking fasteners 26 are then installed to prevent the bone screws 24 from loosening and backing out. Specifically, the threaded shank portion 112 of fastener 26 is engaged within the threaded portion 68 of fastener bore 66 and threaded therethrough by way of a driver (not shown) inserted in tool receiving recess 124. As the locking fastener 26 is driven through fastener bore 66, point 116 pierces the vertebrae and the threaded portion 68 is driven into vertebral bone, thereby further securing plate 22 to upper and lower vertebrae $V_u$, $V_1$. Additionally, by embedding threaded portion 68 in vertebral bone, the locking fastener 26 is less likely to loosen and back out of fastener bore 66. The locking fastener 26 continues to be driven through the fastener bore 66 until the lower conical surface 120 of head portion 110 engages the upper conical surfaces 94 of the bone screws 24. The abutment of locking fastener 26 against bone screws 24 serves to retain bone screws 24 within openings 54, thereby preventing bone screws 24 from loosening and backing out. In an alternative embodiment of the invention, a washer having a lower conical surface may be disposed between the head portion 110 of locking fastener 26 and the head portion 80 of bone screw 24. Tightening the locking fastener 26 would cause the lower conical surface of the washer to engage the upper conical surface 94 of bone screws 24 to retain the bone screws 24 within the openings 54. An example of such a washer is disclosed in U.S. patent application Ser. No. 09/399,525 entitled "Anterior Cervical Plating System" filed on Sep. 20, 1999, the contents of which have been incorporated by reference.

Referring now to FIG. 10, therein is illustrated a stabilization plate 200 according to another embodiment of the present invention. Stabilization plate 200 extends along a longitudinal axis L. Similar to plate 22, stabilization plate 200 is attached to upper and lower vertebrae $V_U$, $V_L$ by way of a plurality of bone screws 24, and a locking screw 26 that engages the heads of adjacent bone screws 24 to prevent bone screws 24 from loosening and backing out. Further details regarding plate 200 are described more fully below. It should be understood that stabilization plate 200 may be used in any application in which the stabilization plate 22 is used, including those specific applications discussed above.

Stabilization plate 200 includes an elongated central portion 202 and a pair of connecting end portions 32 operably attached to opposite ends of central portion 202, such as by welding, fastening, or by any other method known to one of ordinary skill in the art. However, it should be understood that central portion 202 and connection portions 32 can be formed integral to plate 200, thus forming a unitary structure or construct. Central portion 202 is at least partially formed of a shape-memory material that exhibits pseudoelastic characteristics or behavior at about human body temperature. In one embodiment of the invention, the entire plate 200 is formed of the shape-memory material. However, it should be understood that only central portion 202 need be at least partially formed of the shape-memory material, with the connection portion 32 being formed of any suitable bio-compatible material, such as, for example, stainless steel or titanium.

The central portion 202 is at least partially formed of an SMA, such as the SMA described above with regard to plate 22, and has an initial or "memorized" shape or configuration (FIG. 11a), and a different shape or configuration (FIG. 11b) when deformed through the imposition of stress onto plate 200. If the central portion 202 is reshaped or deformed while at a temperature above the transformation temperature $A_s$, the central portion 202 will automatically recover toward its initial shape or configuration when the stress is removed from plate 200. In one embodiment of the present invention, the plate 200 is secured to the upper and lower vertebrae $V_u$, $V_l$ while in a substantially unstressed, initial configuration where virtually all of the SMA material is in an austenitic state. Upon the imposition of stress onto plate 200, caused by relative movement between the upper and lower vertebrae $V_u$, $V_l$, at least a portion of the SMA material is transformed into reversible stress-induced martensite. Upon the reduction or removal of stress, at least a portion of the SMA material is transformed back into austenite. It should be understood that the plate 200 may be pre-stressed prior to being secured to the upper and lower vertebrae $V_u$, $V_1$, thus initially transforming a portion of the SMA material from austenite into SIM. In this case, the SMA material will never attain an entirely austenitic state when the stress imposed onto plate 200 by the upper and lower vertebrae $V_u$, $V_l$ is removed.

Referring specifically to FIG. 11a, central portion 202 is shown in an initial, unstressed configuration. Central portion 202 has a wavy, corrugated shape, defining a series of alternating ridges 204 and grooves 206 extending along longitudinal axis L. Preferably, each of the alternating ridges 204 and grooves 206 is arcuate-shaped so as to form a series of undulating curves extending along longitudinal axis L. Preferably, the ridges 204 and grooves 206 form a sinusoidal pattern relative to the base line B. However, it should be understood that the ridges 204 and grooves 206 can take on other shapes as well, such as, for example, a triangular shape, thus forming a zig-zag pattern, or a square or rectangular shape. When in its initial configuration, central portion 202 has an initial, unstressed length $l_1$, and each of the ridges 204 and grooves 206 defines an initial amplitude $a_l$, as measured from base line B.

Referring now to FIG. 11b, central portion 202 is shown reformed from the initial shape or configuration illustrated in FIG. 11a to a different, stressed shape or configuration, such reformation occurring in response to the imposition of stress caused by relative displacement between the upper and lower vertebrae $V_u$, $V_l$. This relative displacement can arise through translational movement of upper and lower vertebrae $V_u$, $V_l$, as occurring during either flexion or extension of the spinal column, or through torsional movement, as occurring during rotation of the spinal column. The imposition of stress onto central portion 202 causes at least a portion of the shape-memory material to transform into reversible stress-induced martensite. When deformed into its different configuration, central portion 202 has a different, stressed length $l_2$, and the ridges 204 and grooves 206 have a different amplitude $a_2$. In the illustrated embodiment, central portion 202 is elongated or lengthened when stressed, thus increasing length $l_2$ while decreasing the amplitude $a_2$. However, it should be understood that the central portion 202 could alternatively be compressed or shortened when stressed, thus decreasing length $l_2$ while increasing the amplitude $a_2$.

When secured to at least two vertebrae V, stabilization plates 22 and 200 serve to stabilize at least a portion of the spinal column, while allowing at least limited relative displacement or movement between the vertebrae V to restore substantially normal biomechanical function thereto. When secured to the upper and lower vertebrae $V_u$, $V_l$ and stressed in response to relative movement between the upper and lower vertebrae $V_U$, $V_l$, the plates 22, 200 will be reformed from their initial shape or configuration to a different shape or configuration, and at least a portion of the shape-memory material will be transformed from austenite to stress-induced martensite. When in a stress-induced martensitic state, the plates 22, 200 exert a substantially constant restorative force onto the upper and lower vertebrae $V_u$, $V_l$, thereby providing flexible stabilization to the vertebral column, and in particular the cervical region of the spine. Because the plates 22, 200 are at least partially formed of a shape-memory material displaying superelastic or pseudoelastic characteristics, when the stress exerted on plates 22, 200 is reduced or removed, at least a portion of the shape-memory material will transform back into austenite, and the plates 22, 200 will recover toward their initial, memorized shape or configuration. Plates 22, 200 are therefore compliant, capable of being repeatedly transformed between an initial configuration and a different configuration through the imposition and release of stress.

Because the central portions 30, 202 of plates 22, 200 are at least partially formed of a shape-memory material exhibiting pseudoelastic behavior, they are capable of providing a relatively constant restorative forces to the spinal column for correction of various spinal deformities. This pseudoelastic behavior of the shape-memory material allows for a relatively large degree of recoverable deflection or strain of central portion 30, 202 than is possible with conventional materials, such as stainless steel or titanium. For instance, most conventional materials are capable of being elastically deformed over a relatively small range of deflection or strain, and when further stressed begin to deform plastically. However, shape-memory materials are capable of recovering up to about 8% of deflection or strain, well beyond the yield point of conventional materials.

Moreover, because central portions 30, 202 are each configured to define a number of alternating ridges and grooves along the longitudinal axis L of plates 22, 200, when stress is applied, a greater degree of flexation or deflection is possible than with conventional plates having a flat or rectilinear configuration. The spring-like configuration of central portions 30, 202 allows for this added degree of flexibility or compliability. When central portions 30, 202 are in an initial configuration, each has an initial length and the alternating ridges and grooves have an initial amplitude. However, when stress is applied to plates 22, 200 along the longitudinal axis L, central portions 30, 202 will each be reformed to a different configuration defining a different length and amplitude. When the stress is removed, the spring-like action of the central portions 30, 202 will cause each of central portions 30, 202 to recover toward their initial configuration, length and amplitude. By combining the pseudoelastic characteristics of the shape-memory material with the spring-like configuration of central portions 30, 202, greater degrees of flexation or deflection are possible with stabilization system 20 than are currently possible through existing systems.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, although the system 20 has been illustrated and described as a spinal stabilization system, it should be understood that plates 22, 200 can also be used as a connector for connecting a first member to a second member, and need not necessarily be used in conjunction with treatment of the spinal column.

What is claimed is:

1. A device for stabilizing at least a portion of a spinal column, comprising:

a longitudinal member sized to span a distance between at least two vertebral bodies, said longitudinal member being at least partially formed of a shape-memory material, said shape-memory material exhibiting pseudoelastic characteristics at about body temperature;

a plurality of bone anchors for securing said longitudinal member to each of said at least two vertebral bodies; and wherein said longitudinal member stabilizes said portion of the spinal column while allowing at least limited relative displacement between said at least two vertebral bodies, said longitudinal member being reformed from an initial configuration to a different configuration in response to an imposition of stress caused by said relative displacement between said at least two vertebral bodies and recovering toward said initial configuration when said stress is removed.

2. The device of claim 1 wherein said imposition of stress causes at least a portion of said shape-memory material to form stress-induced martensite, and wherein the removal of said stress causes at least a portion of said shape-memory material to form austenite.

3. The device of claim 1 wherein said recovering of said longitudinal member toward said initial configuration occurs without a corresponding change in temperature.

4. The device of claim 1 wherein said longitudinal member is in an austenitic state when in said initial configuration and in a stress-induced martensitic state when in said different configuration.

5. The device of claim 1 wherein said longitudinal member has an initial length when in said initial configuration and a different length when in said different configuration.

6. The device of claim 1 wherein said longitudinal member is a plate having a longitudinal axis, said plate comprising:

a central portion being at least partially formed of said shape-memory material, said central portion having a length extending along said longitudinal axis; and a pair of connection portions disposed adjacent opposite ends of said central portion, each of said connection portions capable of being secured to a respective one of said at least two vertebral bodies by at least one of said plurality of bone anchors.

7. The device of claim 6 wherein said central portion is corrugated along said length.

8. The device of claim 6 wherein said central portion defines a number of alternating ridges and grooves along said longitudinal axis.

9. The device of claim 8 wherein said alternating ridges and grooves have an initial amplitude corresponding to said initial configuration and a different amplitude corresponding to said different configuration.

10. The device of claim 9 wherein said alternating ridges and grooves form a series of undulating curves.

11. The device of claim 6 wherein said central portion comprises:

opposite laterally facing sides;

a number of said alternating ridges and grooves being defined along each of said sides, said ridges and grooves defined along one of said sides being disposed laterally opposite respective ones of said ridges and grooves defined along the other of said sides to form laterally opposing pairs of ridges and laterally opposing pairs of grooves; and a number of openings extending through said central portion and positioned intermediate each of said laterally opposing pairs of ridges.

12. The device of claim 11 wherein said alternating ridges and grooves have an initial amplitude corresponding to said initial configuration and a different amplitude corresponding to said different configuration, and wherein each of said openings has an initial shape corresponding to said initial configuration and a different shape corresponding to said different configuration.

13. The device of claim 11 wherein each of said ridges and grooves has a substantially triangular shape.

14. The device of claim 11 wherein each of said openings is a slot, said slot having sides spanning a distance between said opposing pairs of ridges and defining a slot width therebetween; and wherein said slot has an initial slot width corresponding to said initial configuration and a different slot width corresponding to said different configuration.

15. The device of claim 14 wherein each of said sides of said slot defines a concave surface, said slot being substantially oval-shaped.

16. The device of claim 14 wherein said slot has opposite ends disposed proximately adjacent respective ones of said laterally opposing pairs of ridges.

17. The device of claim 16 wherein said ends of said slot define a partially cylindrical surface.

18. The device of claim 6 wherein said central portion and said connecting portions are integrally formed to define a unitary construct.

19. The device of claim 6 wherein each of said connecting portions comprises:

an inner surface adapted to face said at least two vertebral bodies;

an outer surface facing generally opposite said inner surface; and at least one opening extending between said inner and outer surfaces; and wherein said at least one of said plurality of bone anchors is a bone screw, said bone screw having a head portion and a threaded shank portion, said threaded shank portion being sized to pass through a respective one of said at least one opening and being configured to engage a corresponding one of said vertebral bodies.

20. The device of claim 19 wherein said at least one opening includes an at least partially spherical recess disposed adjacent said outer surface, said head portion having an at least partially spherical surface substantially complementary to said recess.

21. The device of claim 19 wherein each of said connecting portions further comprises:
a bore extending from said outer surface toward said inner surface and being disposed adjacent said at least one opening; and
a locking device disposed within said bore and being adapted to engage said head portion of said bone screw disposed within said respective one of said at least one opening.

22. The device of claim 21 wherein said locking device is a fastener, said fastener having:
a shank portion adapted to be engaged within said bore; and
a head portion having a lower surface being substantially complementary to an upper surface of said head portion of said bone screw disposed within said respective one of said at least one opening.

23. The device of claim 22 wherein said lower surface of said fastener and said upper surface of said bone screw are each conical shaped.

24. The device of claim 19 wherein each of said connecting portions includes an inner surface adapted to face said at least two vertebral bodies and forming a concave lateral curvature extending along said longitudinal axis.

25. A device for stabilizing at least a portion of a spine, comprising:
a compliant element at least partially formed of a pseudoelastic shape-memory material displaying reversible stress-induced martensitic behavior at about human body temperature, said compliant element having a longitudinal axis and a length sized to span a distance between at least two spinal motion segments;
at least two anchoring elements, each adapted to engage a respective one of said at least two spinal motion segments to secure said compliant element thereto; and
wherein said length of said compliant element is variable between an initial length and a different length through an imposition of stress caused by relative displacement between said at least two spinal motion segments, said different length occurring through a transformation of at least a portion of said pseudoelastic shape-memory material into reversible stress-induced martensite, and wherein said compliant element recovers toward said initial length when said stress is removed.

26. The device of claim 25 wherein said compliant element provides stabilization to said at least two spinal motion segments while restoring substantially normal biomechanical function thereto.

27. The device of claim 25 wherein said at least a portion of the spine is in the cervical region of the spine.

28. The device of claim 25 wherein said different length of said compliant element is greater than said initial length.

29. The device of claim 25 wherein said compliant element has an initial configuration corresponding to said initial length and a different configuration corresponding to said different length.

30. The device of claim 29 wherein said compliant element defines a plurality of alternating ridges and grooves dispersed along said longitudinal axis, said ridges and grooves having an initial amplitude corresponding to said initial length and a different amplitude corresponding to said different length.

31. The device of claim 30 wherein said alternating ridges and grooves form a series of undulating curves extending along said longitudinal axis.

32. The device of claim 30 wherein said initial amplitude is greater than said different amplitude.

33. The device of claim 30 wherein said compliant element has an accordion-like shape.

34. The device of claim 25 wherein said compliant element includes at least one opening extending therethrough in a direction transverse to said longitudinal axis, said at least one opening having an initial shape corresponding to said initial length and a different shape corresponding to said different length.

35. The device of claim 34 wherein said at least one opening is a slot having a length extending substantially perpendicular to said longitudinal axis and having a width that varies relative to a corresponding change is said length.

36. The device of claim 35 wherein said slot is substantially oval-shaped.

37. The device of claim 25 wherein said compliant element includes a pair of laterally opposing thin sections of material connected by a plurality of laterally extending linking portions, each of said sections of material defining a number of alternating ridges and grooves along said longitudinal axis, said ridges and grooves defined by one of said sections of material being disposed laterally opposite respective ones of said ridges and grooves defined by the other of said sections of material to form laterally opposing pairs of ridges and laterally opposing pairs of grooves, each of said linking portions extending between said laterally opposing pairs of grooves.

38. The device of claim 37 wherein said alternating ridges and grooves have an initial amplitude corresponding to said initial length and a different amplitude corresponding to said different length.

39. The device of claim 37 wherein each of said alternating ridges and grooves has a substantially triangular shape.

40. A spinal stabilization system, comprising:
an elongate member for placement adjacent a cervical region of the spine, said elongate member being at least partially formed of a pseudoelastic shape-memory material, said shape-memory material displaying reversible stress-induced martensitic behavior at about human body temperature;
at least two bone engaging members each adapted to engage a respective one of at least two cervical vertebrae to secure said elongate member thereto; and
wherein said elongate member is deformed during relative displacement between said at least two cervical vertebrae, said deformation of said elongate member transforming a portion of said shape-memory material into a stress-induced martensitic state, said elongate member exerting a substantially constant restorative force on said at least two cervical vertebrae when said shape-memory material is in said stress-induced martensitic state to thereby flexibly stabilize said cervical region of the spine.

41. The system of claim 40 wherein said relative displacement between said at least two cervical vertebrae occurs during either flexional or extensional movement of said cervical region of the spine.

42. The system of claim 40 wherein said relative displacement between said at least two cervical vertebrae occurs during torsional movement of said cervical region of the spine.

43. The system of claim 40 wherein said elongated member has a length adapted to extend between said at least two cervical vertebrae, said deformation of said elongate member causing said length to be varied between an initial length and a different length.

44. The system of claim 43 wherein said elongate member has an initial shape corresponding to said initial length and a different shape corresponding to said different length.

45. A connector apparatus for connecting a first member to a second member, comprising:

a deformable central portion having a longitudinal axis and being at least partially formed of a shape-memory material, said shape-memory material exhibiting pseudoelastic characteristics at about body temperature, said central portion defining a number of alternating ridges and grooves along said longitudinal axis; and at least two connection portions, each of said connection portions being disposed adjacent opposite ends of said central portion and being configured to engage a respective one of the first and second members; and wherein said alternating ridges and grooves are transformed from an initial configuration to a different configuration in response to an imposition of stress caused by relative displacement between the first and second members and reformed toward said initial configuration when said stress is removed.

46. The apparatus of claim 45 wherein central portion has an initial length when in said initial configuration and a different length when in said different configuration.

47. The apparatus of claim 46 wherein said alternating ridges have an initial amplitude corresponding to said initial configuration and a different amplitude corresponding to said different configuration.

48. The apparatus of claim 45 wherein said central portion is corrugated along said longitudinal axis.

49. The apparatus of claim 48 wherein said central portion has an accordion-like shape.

50. The apparatus of claim 45 wherein each of said connection portions are disposed along said longitudinal axis.

51. A method for stabilizing at least a portion of a spinal column, comprising:

providing an elongate member having a length extending between at least two vertebrae and being at least partially formed of a pseudoelastic shape-memory material, the pseudoelastic shape-memory material displaying reversible stress-induced martensitic behavior at about body temperature;

securing the elongate member to the at least two vertebrae;

transforming at least a portion of the shape-memory material into a stress-induced martensitic state as a result of an imposition of stress onto the elongate member during relative movement between the at least two vertebrae; and applying a substantially constant restorative force to the at least two vertebrae when the shape-memory material is in the martensitic state to provide stabilization to the at least a portion of the spinal column.

52. The method of claim 51 wherein the transforming is accompanied by a corresponding change in the length of the elongate member.

53. The method of claim 52 wherein the change in length of the elongate member is accompanied by a corresponding change in shape of the elongate member.

54. The method of claim 51 wherein the relative movement between the at least two vertebrae occurs during translational flexion and translational extension of the spinal column.

55. The method of claim 51 wherein the relative movement between the at least two vertebrae occurs during torsional rotation of the spinal column.

* * * * *